United States Patent [19]
Elsberry et al.

[11] Patent Number: 5,725,017
[45] Date of Patent: Mar. 10, 1998

[54] IN-LINE PRESSURE CHECK VALVE FOR DRUG-DELIVERY SYSTEMS

[75] Inventors: Dennis D. Elsberry, New Hope; Richard H. Comben, St. Paul, both of Minn.

[73] Assignee: Medtronic, Inc., Minneapolis, Minn.

[21] Appl. No.: 789,693

[22] Filed: Jan. 27, 1997

[51] Int. Cl.$^6$ ............................................. F16K 15/00
[52] U.S. Cl. ................................... 137/517; 137/529
[58] Field of Search ................................. 137/517, 529, 137/859; 604/247; 251/368

[56] References Cited

U.S. PATENT DOCUMENTS

| | | | |
|---|---|---|---|
| 2,097,585 | 11/1937 | Carson | 137/529 |
| 3,032,060 | 5/1962 | Huffman | 137/529 |
| 3,474,783 | 10/1969 | Ulmann | 137/529 |
| 3,608,574 | 9/1971 | Beaussant | 137/529 |
| 4,846,215 | 7/1989 | Barree | 137/859 |
| 4,852,605 | 8/1989 | Gouhier | 137/859 |
| 5,097,865 | 3/1992 | Riley | 137/529 |
| 5,232,012 | 8/1993 | Toraason | 137/859 |
| 5,265,645 | 11/1993 | Goodwin | 137/859 |

*Primary Examiner*—Denise L. Ferensic
*Assistant Examiner*—Joanne Y. Kim

*Attorney, Agent, or Firm*—Curtis D. Kinghorn; Harold R. Patton

[57] ABSTRACT

A pressure control valve, fabricated using micromachining techniques, comprises, in one embodiment a substrate having a central orifice therein and having a sealed chamber formed therein, one wall of which being defined by a flexible membrane. An inlet control element is supported by the membrane such that it is disposed over the central orifice, such that normally a gap is defined between the inlet control element and the central orifice and hence the valve is open. When the pressure differential, between external pressure and pressure in the chamber, exceeds a predetermined threshold, the membrane deforms, drawing the inlet control element toward the substrate such that the inlet control element seats over the central orifice, closing the valve. In another embodiment a flexible membrane cooperates with a valve substrate to form a closed chamber, and a valve lid, coupled to the membrane, extends over one or more holes in the substrate, forming a gap between the valve lid and the substrate. When a predetermined level of pressure is applied to the valve lid, the gap closes, preventing fluid from flowing through the hole(s). Valves in accordance with the present invention may be micromachined from such materials as glass or metal, and may be incorporated in-line in the filling conduit for the reservoir of an implantable drug delivery system.

8 Claims, 4 Drawing Sheets

IN-LINE PRESSURE CHECK VALVE FOR DRUG-DELIVERY SYSTEMS

FIELD OF THE INVENTION

This invention relates generally to the field of medical devices, and more particularly relates to an implantable drug delivery system.

BACKGROUND OF THE INVENTION

It has been shown in the prior art that it is possible to implement a body-implantable apparatus operable to deliver a fluid therapeutic agent to a desired location within a human body on a long-term basis.

U.S. Pat. No. 3,527,220, for example, proposes an implantable drug administrator which operates with a refillable bladder reservoir and a roller pump driven by a magnet located outside the body.

U.S. Pat. No. 3,951,147 describes a reservoir formed from a bellows enclosed within a housing. The contents of the reservoir are pressurized by a fluorocarbon fluid located in the space between the housing and the bellows. The unit continuously dispenses the liquid to the body site through a capillary tube.

U.S. Pat. No. 4,692,147 to Duggan discloses a body-implantable electronic drug administration device comprising a peristaltic (roller) pump for metering a measured amount of drug in response to an electronic pulse generated by control circuitry associated with the device. The Duggan '147 patent is hereby incorporated by reference herein in its entirety.

The efficacy and commercial viability of implantable drug administration devices is well-proven. The Synchromed™ and Infusaid™ infusion pumps, commercially available from Medtronic, Inc., Minneapolis, Minn., and Pfizer, Inc, Norwood, Mass., respectively, are examples of current state-of-the-art implantable drug delivery systems.

Precise drug delivery from an implantable drug infusion pumping system requires controlled conditions during charging of the reservoir with a therapeutic agent, to prevent excessive reservoir pressure which can lead to excessive, out-of-specification drug infusion rates. Current drug infusion systems, such as the Synchromed™ and Infusaid™ operate with a positive pressure drug reservoir. An over-pressurization of the reservoir can occur depending upon the filling pressure.

To overcome this problem, an external pressure monitoring device has been included as component of a refill kit for a drug delivery system to provide the user with a means for detecting an overpressurization condition. More recently, an overpressurization device consisting of a valve and valve seat incorporated into the reservoir refill septum column has been proposed. See, e.g., U.S. Pat. No. 5,158,547 to Phong Doan et al., entitled "Drug Administration Device Over Full Protection Valve." The Doan '547 patent is hereby incorporated by reference herein in its entirety.

Another approach proposed in the Doan '547 patent is a spring-loaded valve actuator. The design proposed by Doan includes valve seats fixed to the fill tube channel of an implantable drug delivery device. As the designated reservoir volume is reached, the spring-actuated valve closes into the fill tube channel valve seat.

Another proposed design consists of a pressure control valve which is normally open until pressure reaches a specified level. See co-pending U.S. patent application Ser. No. 08/422,362 filed in the name of Shoberg and Heruth, entitled "Pressure Controlled System for Filling an Implantable Drug Infusion System." Shoberg and Heruth propose fabricating the valve using micromachining techniques. A calibrated spring produces the desired valve closure pressure. It is believed that constraints upon the size of an implantable device may, under some circumstances, render the Shoberg and Heruth valve impractical.

Micromachining technology has been shown to be useful in the fabrication of miniaturized, unidirectional flow valves and piezoelectric from silicon and Pyrex glass. For example, U.S. Pat. No. 4,869,282 to Sittlier et al., entitled "Micromachined Valve With Polyimide Film Diaphragm" proposes a micromachined miniature valve for use in gas chromatography. The Sittler et al. valve is normally closed, and is actuated to open and permit fluid flow through pressure exerted via an actuator port. Similarly, in U.S. Pat. No. 4,756,508 to Giachino et al., entitled "Silicon Valve," there is proposed a normally closed silicon valve for controlling the flow of fluid. The Giachino et al. valve is actuated by an electrical signal.

The Sittler et al., Giachino et al. and Saaski references demonstrate the feasibility and utility of fabricating miniature valves and the like using micromachining techniques such as photolithography, etching, electrostatic discharge machining, and the like. The devices proposed by Sittler et al., Giachino et al. and Saaski appear to be capable only of controlling the flow rate of fluid therethrough, however, and not of controlling the pressure in a sealed compartment.

Both current and future implantable drug delivery device designs require miniaturization of internalized pressure control mechanisms. Such valves may also find application in catheter access ports.

SUMMARY OF THE INVENTION

In view of the foregoing considerations, the present invention is directed to a miniaturized, normally open in-line pressure check valve fabricated using micromachining techniques.

In one embodiment, micromachining techniques are used to form valves from Pyrex glass or silicon with metallized valve seats. The micromachined components can be assembled into a completed valve using anodic bonding techniques. The pressure check valve in accordance with the present invention may be positioned in-line in the fluid compartment (reservoir) to be pressure controlled. The desired pressure required for valve actuation is determined by the force required to deform a silicon membrane, which in turn is determined by the thickness of such membrane.

In one embodiment, the valve comprises a substrate having a central orifice therein, and having a sealed chamber therein with one wall of the chamber being defined by a flexible membrane. The valve in this embodiment further comprises an inlet control element that is supported by the membrane such that the inlet control element is disposed above the central orifice and defines a gap between itself and the substrate. In this state, fluid can pass through the valve as a result of the gap between the inlet control element and the substrate.

The valve is actuated automatically when external pressure exceeds a predetermined threshold. When the pressure differential between external pressure and pressure in the chamber of the substrate exceeds a threshold value, the membrane deforms inward and draws the inlet control element down to seat on top of the substrate, eliminating the gap and preventing passage of fluid through the central orifice of the substrate.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF SPECIFIC EMBODIMENTS OF THE INVENTION

Figure 1:
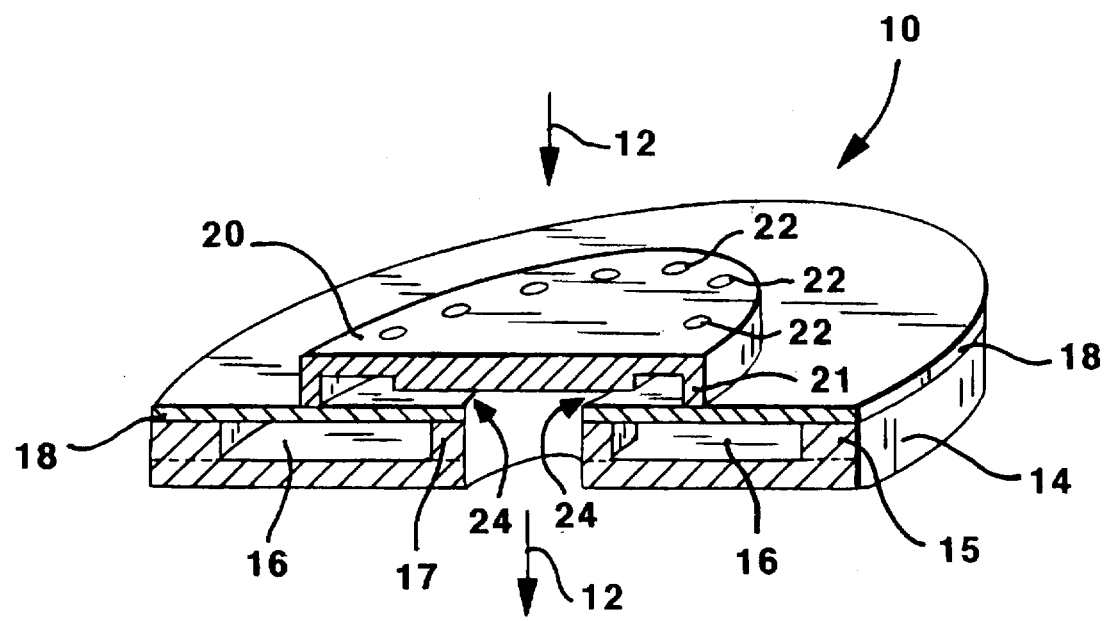
FIG. 1 is a cut-away perspective view of a miniature pressure check valve in accordance with one embodiment of the invention.

A presently preferred embodiment of a normally-open, in-line pressure check valve 10 in accordance with the present invention is illustrated in the cut-away perspective view of FIG. 1. The direction of fluid flow through valve 10 is indicated by arrows 12 in FIG. 1.

Figure 2:
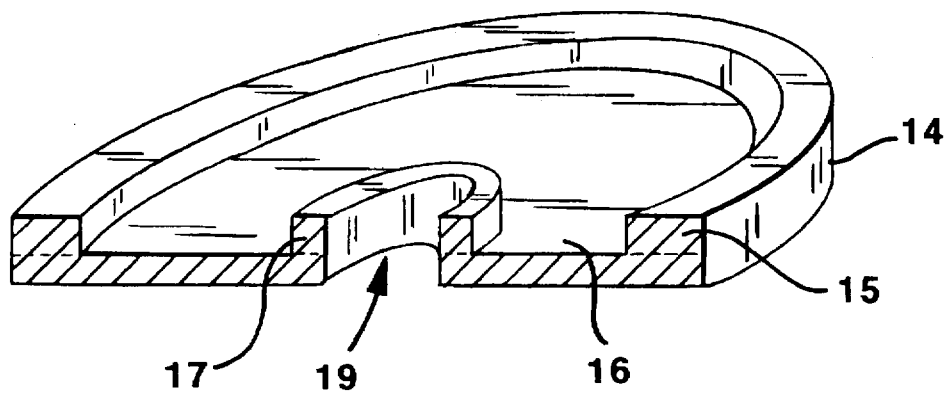
FIG. 2 is a cut-away perspective view of the substrate of the valve from FIG. 1.

Valve 10 comprises a substantially annular substrate 14 which, in the presently preferred embodiment of the invention is micromachined from Pyrex glass or the like. In the embodiment of FIG. 1, substrate 14 has a first annular projection 15 around its circumference and a second annular projection 17 surrounding its central orifice 19. This can perhaps be best appreciated with reference to FIG. 2, which shows only substrate 14 and annular projections 15 and 17. (In the Figures, dashed lines are used to indicate the boundary between substrate 14 and annular projections 15 and 17; it is to be understood, however, that in the presently preferred embodiment of the invention, annular projections 15 and 17 are integral with substrate 14. The dashed lines are intended merely add clarity to this disclosure.) Annular projections 15 and 17 and substrate 14 together function to define the sides and bottom of a chamber designated with reference numeral 16.

Figure 3:
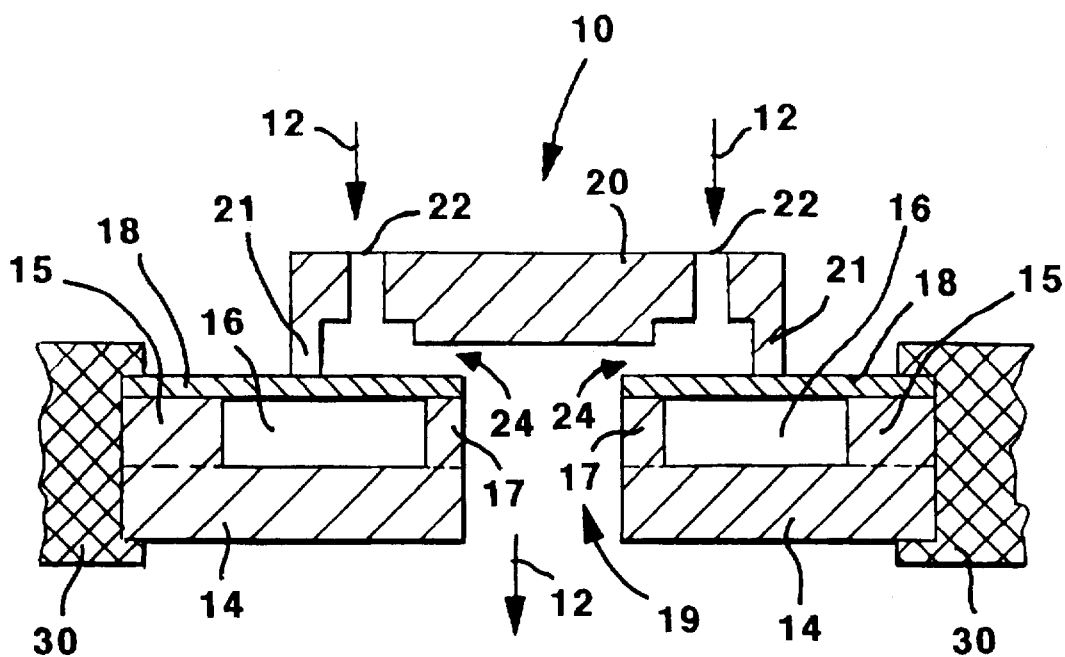
FIG. 3 is a cross-sectional view of the valve from FIG. 1, shown in an open state.

With continued reference to FIG. 1, and also with reference to FIG. 3, which shows valve 10 in cross-section, valve 10 further comprises an flexible annular membrane 18 disposed on top of substrate 14. Annular membrane 18 defines the top of chamber 16, and renders chamber 16 air-tight. In one embodiment, membrane 18 is made of silicon and is anodically bonded onto substrate 14.

An inlet control element 20 is disposed on top of and is supported by membrane 18. Inlet control element 20 is also preferably fabricated from Pyrex glass or the like using micromachining techniques. In one embodiment, inlet control element 20 is anodically bonded to membrane 18. A plurality of holes 22 are formed in inlet control element 20 to enable fluid to pass therethrough.

Normally, i.e., when there is no differential between the external pressure and the pressure within chamber 16, valve 10 is in the state shown in FIGS. 1 and 3, such that there is a gap, designated with reference numeral 24, between the underside of inlet control element and the top of membrane 18. The existence of gap 24 arises as a result of annular projection 21 on the underside of inlet control element 20. In the open state of FIG. 3, fluid is allowed to flow through valve 10, entering through holes 22 in inlet control element, flowing through gap 24, and out via central orifice 19 in substrate 14.

Figure 4:
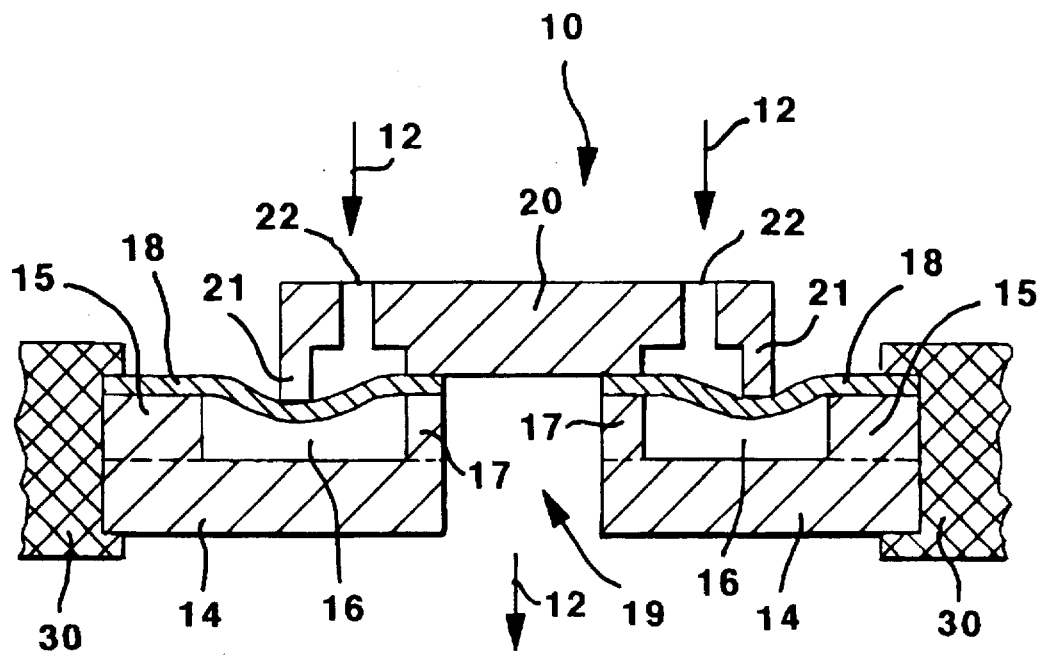
FIG. 4 is a cross-sectional view of the valve from FIG. 1 shown in a closed state.

When the external pressure in the environment in which valve 10 is disposed increases above the pressure in chamber 16, however, this pressure differential causes membrane 18 to deform. Such deformation results in a proportional decrease in the height of gap 24, since inlet control element 20 is affixed to and supported by membrane 18. When the external pressure reaches the rated pressure of valve 10, which can be controlled by controlling the thickness of membrane 18, valve closure occurs. Valve 10 in a closed state is illustrated in cross section in FIG. 4; in this closed state, the underside of inlet control element 20 is seated over orifice 19 in substrate 14. In this closed state of FIG. 4, fluid is thus prevented from passing through valve 10.

It is to be noted that valve 10 is advantageously actuated only under over-pressurized conditions; this feature will tend to enhance the valve's functional longevity.

Figure 5:
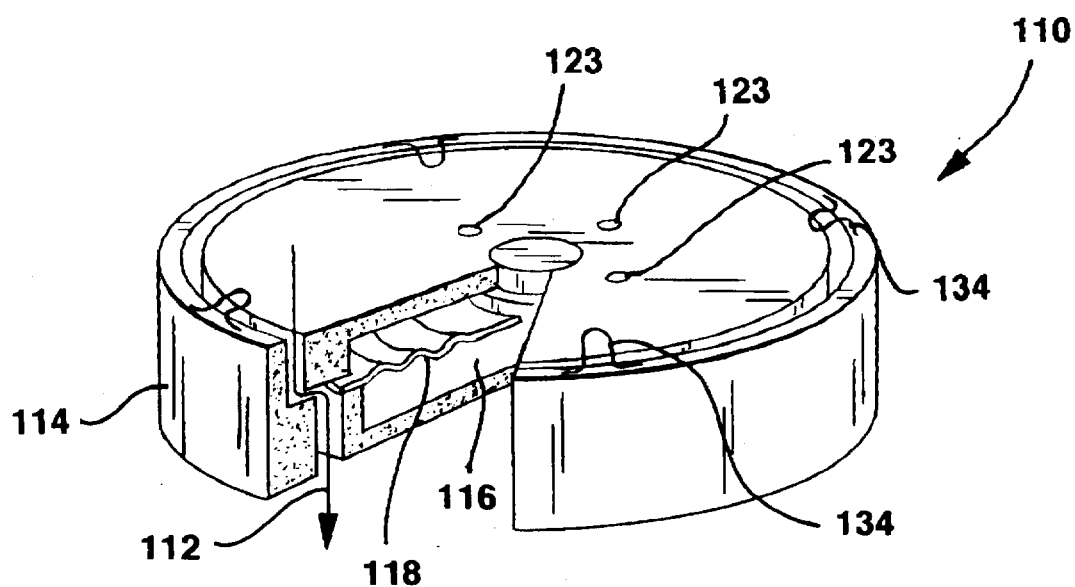
FIG. 5 is a cut-away perspective view of a minature pressure check valve in accordance with another embodiment of the invention.
Figure 6:
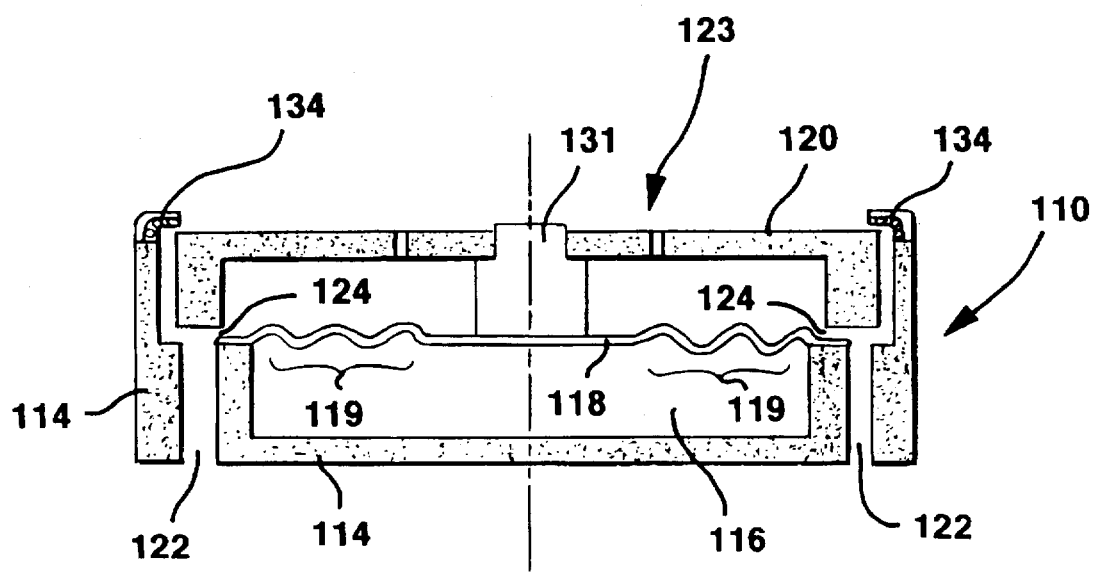
FIG. 6 is a cross-sectional view of the valve from FIG. 5.
Figure 7:
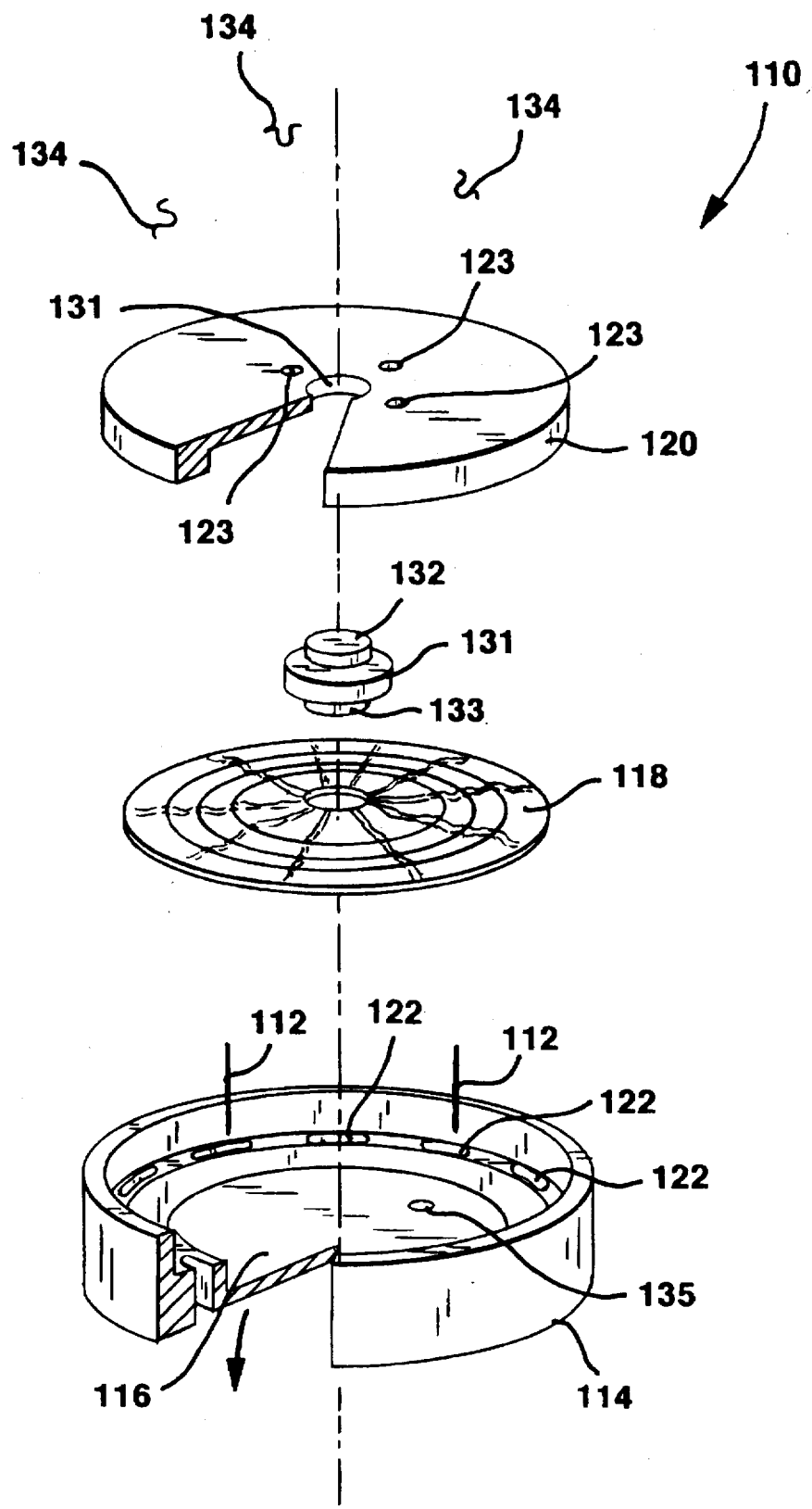
FIG. 7 is an exploded perspective view of the valve from FIG. 5.

Turning now to FIGS. 5-7, there is shown an alternative embodiment of the invention. For the embodiment of FIGS. 5-7, machining techniques may be used to form valve components from metal, such as titanium. The components may then be assembled into a completed valve using laser welding techniques or the like.

The pressure valve designated with reference numeral 110 in FIGS. 5-7 differs from the embodiment of FIGS. 1-4 in that fluid inlet and outlet valve seating surfaces are disposed generally near the periphery of the valve body rather than centrally located.

The direction of fluid flow through valve 110, which is normally open, is indicated by arrows 112 in FIGS. 5-7. Inlet holes 123 allow fluid wash across a corrugated flexible annular membrane 18, as will be hereinafter described in further detail.

Valve 110 comprises four components which are preferably made of metal, e.g., titanium: an upper valve lid 120 defining an upper surface of valve gap 124; a spacer 131 adapted to be affixed at a top surface 132 (for example, by laser welding) to valve lid 120; a corrugated membrane 118, affixed (again, for example, by laser welding) to a bottom surface 133 of spacer 131; membrane 118 is also coupled to a lower valve substrate 114 that a lower surface of valve gap 124. Lower valve substrate 114 has a plurality of holes 122 therein providing a path for fluid to flow through valve 110 in the direction of arrows 112. In the presently disclosed embodiment, holes 122 are disposed generally around the circumference of substrate 114.

Although four components are referred to herein, it is contemplated that valve lid 120 and spacer 131 may be integrally formed. It is believed that this design variant would be readily understood by those of ordinary skill in the art.

Membrane 118 is joined circumferentially (for example, by laser welding) to lower valve substrate 114, and thereby cooperates with lower valve substrate to form a closed chamber 116, as shown in FIG. 6.

The corrugations 119 of membrane 118 enable membrane 118 to flex and be displaced downward into chamber 116. Since membrane 118 is affixed to upper valve lid 120 (either via spacer 131 or directly, if valve lid 120 and spacer 131 are integrally formed), such flexure draws valve lid 120 downward, thereby closing valve gap 124. Stops 134 are preferably disposed around the upper circumference of lower valve substrate 124 to provide an upper limit to the travel of valve lid 120, hence establishing a maximum size of valve gap 124.

In the embodiment of FIGS. 5–7, as in the embodiment of FIGS. 1–4, the principle of valve closure is dependent upon fluid flow through valve 110 exerting sufficient force upon valve lid 120 to exceed the deformation force of diaphragm 118 and the internal pressure of chamber 116. Pressure exerted on valve lid 120 is applied to membrane 118 via spacer 131. When sufficient force is applied to valve lid 120 and hence to diaphragm 118, diaphragm 118 flexes and is displaced into chamber 116, thereby drawing valve lid 120 down. Ultimately, if sufficient pressure is applied, valve lid 120 is drawn down to such an extent that valve gap 24 is completely closed. Since valve lid 120 is disposed over holes 122, when valve gap 24 is closed, holes 122 are sealed.

As with the embodiment of FIGS. 1–4, in the embodiment of FIGS. 5–7, the amount of pressure necessarily applied to valve lid 120 in order for valve 110 to close is determined in part by the pressure within chamber 116. That is, the threshold pressure of valve 110 changes with changing pressure within chamber 116. It is contemplated that the pressure within chamber 116 can be controlled during manufacture of valve 110, such that the desired threshold pressure for valve 110 can be selected. For example, in one embodiment, an access hole 135 is provided for controlling the pressure in chamber 116; hole 135 may then be sealed to retain the desired pressure therein.

In-one embodiment, valve 110 has an approximate diameter of 1.0 cm and an approximate height of 0.5 cm.

Stops 134 are affixed around the upper circumference of lower substrate 114 to impose an upper limit on the displacement of upper valve lid 120, and hence on the size of valve gap 124.

It is contemplated that a miniature valve in accordance with the present invention can be advantageously utilized in numerous different applications. As noted above, however, a valve in accordance with the present invention is believed to be particularly beneficial in one application in particular, namely implantable drug delivery devices. A valve such as valve 10 described herein can be advantageously disposed in-line in the drug input port to an implantable drug delivery device's drug reservoir, in order to ensure that the pressure in the reservoir does not exceed a predetermined limit.

Several different methods of disposing a valve in accordance with the present invention in-line in a fluid conduit are contemplated. For valve 10 described herein, for example, the valve could be secured within an annular gasket, so that the gasket and valve assembly can be introduced into a fluid conduit. Alternatively, conventional ceramic-to-metal processing can be used to form a metal-to-metal feedthrough ring which can be welded in-line.

What is claimed is:

1. A pressure control valve, comprising:

a substrate having a central orifice therein;

a flexible membrane defining one wall of a sealed chamber formed in said substrate;

an inlet control element, disposed over said orifice and supported by said membrane such that a gap is normally defined between said inlet control element and said substrate;

wherein a pressure differential, between external pressure and pressure in said chamber, results in deformation of said membrane such that said inlet control element is drawn toward said substrate, thereby eliminating said gap and closing said valve.

2. A pressure control valve in accordance with claim 1, wherein said substrate and said inlet control element are micromachined from glass.

3. A pressure control valve in accordance with claim 2, wherein said membrane is silicon.

4. A pressure control valve, comprising:

a substrate having a central orifice therethrough, and having a sealed chamber therein with said chamber's top being defined by a flexible membrane;

an inlet control element, coupled around its perimeter to said membrane such that said inlet control element is disposed above said central orifice, and normally defines a gap between said inlet control element and said substrate, said inlet control element having a plurality of holes therethrough;

said valve normally having a fluid path therethrough whereby fluid enters through said plurality of holes, passes through said gap, and exits through said central orifice;

wherein a pressure differential, between external pressure and pressure in said chamber, above a predetermined threshold, causes deformation of said membrane, drawing said inlet control element toward said substrate and eliminating said gap, such that said fluid path is interrupted.

5. A pressure control valve having a normally open configuration and a closed configuration, said valve comprising:

a substrate, having at least one hole therein providing a fluid path through said valve;

a flexible membrane, coupled to said substrate; and a valve lid, coupled to said membrane such that pressure exerted on said valve lid is applied to said membrane, said membrane flexing in response to such pressure, said valve lid extending over said at least one hole in said substrate;

wherein when no pressure is applied to said valve lid, a valve gap is defined between said valve lid and said substrate, such that fluid is permitted to flow through said at least one hole;

and wherein when pressure applied to said valve lid causing said membrane to flex draws said valve lid toward said membrane, said valve gap narrows, such that pressure above a predetermined level applied to said valve lid closes said gap and prevents fluid from flowing through said at least one hole.

6. A pressure control valve in accordance with claim 5, wherein said substrate and said valve lid are made of metal.

7. A pressure control valve in accordance with claim 6, wherein said metal is titanium.

8. A pressure control valve in accordance with claim 5, wherein said membrane and said substrate cooperate to form a closed chamber, and wherein said predetermined pressure level changes with changes in pressure in said closed chamber.

* * * * *